(12) United States Patent
Wartini et al.

(10) Patent No.: US 7,439,406 B2
(45) Date of Patent: Oct. 21, 2008

(54) METHOD FOR HYDROGENATING METHYLOL ALKANALS

(75) Inventors: Alexander Wartini, Heidelberg (DE); Matthias Dernbach, Dossenheim (DE); Steffen Maas, Bubenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 345 days.

(21) Appl. No.: 10/553,195

(22) PCT Filed: Apr. 14, 2004

(86) PCT No.: PCT/EP2004/003951

§ 371 (c)(1), (2), (4) Date: Oct. 13, 2005

(87) PCT Pub. No.: WO2004/092097

PCT Pub. Date: Oct. 28, 2004

(65) Prior Publication Data

US 2006/0205985 A1  Sep. 14, 2006

(30) Foreign Application Priority Data

Apr. 16, 2003  (DE) ............................... 103 17 543

(51) Int. Cl.
- *C07C 29/14* (2006.01)
- *C07C 31/20* (2006.01)
- *C07C 45/45* (2006.01)
- *C07C 31/18* (2006.01)

(52) U.S. Cl. ............ 568/881; 568/853; 568/464; 568/862; 568/463; 568/457; 568/458

(58) Field of Classification Search ........... 568/853, 568/881, 464, 862, 463, 457, 458
See application file for complete search history.

(56) References Cited

U.S. PATENT DOCUMENTS 5,146,012 A * 9/1992 Salek et al. ............ 568/881
5,185,478 A * 2/1993 Salek et al. ............ 568/853
5,532,417 A * 7/1996 Salek et al. ............ 568/853

FOREIGN PATENT DOCUMENTS

| DE | 1 941 633 | 3/1971 |
| DE | 1 957 591 | 5/1971 |
| DE | 2 040 501 | 2/1972 |
| DE | 25 07 461 | 9/1976 |
| EP | 044 444 | 1/1982 |
| EP | 522 368 | 1/1993 |
| WO | 92/22521 | 12/1992 |
| WO | 95/32171 | 11/1995 |
| WO | 97/17313 | 5/1997 |
| WO | 98/28253 | 7/1998 |
| WO | 98/29374 | 7/1998 |
| WO | 01/51438 | 7/2001 |

* cited by examiner

*Primary Examiner*—Elvis O. Price
(74) *Attorney, Agent, or Firm*—Oblon, Spivak, McClelland, Maier & Neustadt, P.C.

(57) ABSTRACT

Disclosed is a method for the catalytic hydrogenation of methylol alkanals of general formula (I), where $R^1$ and $R^2$ independently represent an additional methylol group or an alkyl group having with 1 to 22 carbon atoms, or an alkyl group with 1 to 22 C atoms, or an aryl group or aralkyl group with 6 to 33 carbon atoms, in the liquid phase on a hydrogenation catalyst. The inventive method is characterized in that a pH value ranging between 6.3 and 7.8 is adjusted in the hydrogenation feed by adding at least one tertiary amine

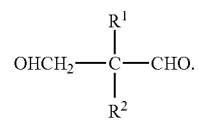

9 Claims, No Drawings

METHOD FOR HYDROGENATING METHYLOL ALKANALS

The present invention relates to a process for the catalytic hydrogenation of methylol-alkanals in the liquid phase over a hydrogenation catalyst at a pH of the hydrogenation feed which has been set to from 6.3 to 7.8 by addition of tertiary amine.

The catalytic hydrogenation of carbonyl compounds such as aldehydes for preparing simple and functional alcohols occupies an important position in the production streams of the basic chemicals industry. This is particularly true of the hydrogenation of aldehydes which are obtainable via the oxo process or aldol reaction.

The aldol reaction of alkanals with excess formaldehyde in the presence of stoichiometric amounts of base produces methylolalkanals. The use of inorganic hydroxides such as sodium hydroxide or calcium hydroxide as base is known from WO 01/51438. WO 98/28253 describes amines as basic catalysts in the aldol reaction and WO 98/29374 describes basic ion exchangers for this purpose. In these processes, the methylolalkanal is obtained as a 20-70% strength by weight aqueous solution. The pH of this aqueous solution is only 3.5-6.0, since the basic catalyst used for the aldol reaction also catalyzes the Cannizzaro reaction of formaldehyde to form formic acid which in turn at least partly neutralizes the base.

If polyhydric alcohols such as pentaerythritol, neopentyl glycol or trimethylolpropane are to be prepared from aqueous methylolalkanal solutions, these solutions have to be hydrogenated.

This hydrogenation is generally carried out at above 80° C. Redissociation of the methylol group to the free aldehyde and also ether, ester and acetal formation are observed in the hydrogenation reactor. These secondary reactions lead to low hydrogenation selectivities and to low yields of the polyhydric alcohols.

In addition, many hydrogenation catalysts are not stable under these conditions. Catalysts based on oxides of aluminum and silicon in particular, as are known from EP-A 44 444 and WO 95/32171, lose at least some of the hardness in these aqueous methylolalkanal solutions under hydrogenation conditions due to leaching of silicon dioxide and in the worst case become unusable.

It is an object of the present invention to provide a process for the catalytic hydrogenation of methylolalkanals in which redissociation of methylolalkanals formed is largely suppressed, the formation of ethers, esters and acetals is largely prevented and a positive effect is exerted on the mechanical stability of the catalyst. In addition, the process should make it possible to obtain polyhydric alcohols with good hydrogenation selectivities and in good yields.

We have found that this object is achieved by a process for the catalytic hydrogenation of methylolalkanals of the formula

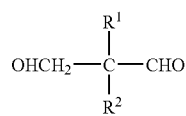

where $R^1$ and $R^2$ are each, independently of one another, a further methylol group or an alkyl group having from 1 to 22 carbon atoms or an aryl or aralkyl group having from 6 to 33 carbon atoms, in the liquid phase over a hydrogenation catalyst, wherein the pH of the hydrogenation feed is set to from 6.3 to 7.8 by addition of at least one tertiary amine.

The hydrogenation feed referred to in the present patent application is an aqueous solution comprising a methylolalkanal of the formula 1, in particular an aqueous solution comprising from 20 to 80% by weight of methylolalkanal. Such a hydrogenation feed is preferably prepared as described in WO 98/28253 by condensation of aldehydes with formaldehyde.

In this reaction, the aldehyde is reacted with from 2 to 8 times its amount of formaldehyde in the presence of a tertiary amine (aldol formation) and the reaction mixture is separated into two solutions of which one comprises the methylolalkanal mentioned and the other comprises unreacted starting material. The latter solution is returned to the reaction. The fractionation is achieved by distillation or by simple separation of the aqueous phase from the organic phase. The aqueous solution comprising the methylolalkanal can be used as hydrogenation feed in the process of the present invention.

However, it is also possible to prepare the aqueous methylolalkanal solution as hydrogenation feed by other processes of the prior art, for example by the processes known from WO 01/51438, WO 97/17313 and WO 98/29374.

In a preferred variant of the process of the invention, an aqueous methylolalkanal solution which is particularly low in formaldehyde or is free of formaldehyde is used as hydrogenation feed. In a methylolalkanal solution referred to as low in formaldehyde, the formaldehyde content is less than 5% by weight. Formaldehyde can be separated off from the output from the aldol formation reaction, which has been obtained, for example, as described in WO 98/28253, by methods known from the prior art, for example by distillation.

The methylolalkanal of the formula I is preferably a dimethylolalkanal, pentaerythrose or hydroxypivalaldehyde.

The hydrogenation feed is mixed with tertiary amine upstream of the inlet of the hydrogenation reactor until the hydrogenation feed has a pH of from 6.3 to 7.8. It is also possible to feed the hydrogenation feed and the tertiary amine separately into the reactor and mix them there.

Suitable tertiary amines are, for example, the amines listed in DE-A 25 07 461. Preferred tertiary amines are tri-n-$C_1$-$C_4$-alkylamines, particularly preferably trimethylamine, triethylamine, tri-n-propylamine and tri-n-butylamine.

Amines are particularly advantageous for adjusting the pH, since they form thermally decomposable salts with formic acid so that the salts can be dissociated again after the hydrogenation. In this way, a salt as coproduct can be avoided and the tertiary amine can be returned to the process.

It is particularly advantageous to use the same tertiary amine in the aldol formation process which produces the methylolalkanal, viz. the condensation of a higher aldehyde and formaldehyde, and in the hydrogenation. The pH is measured by known methods, preferably by means of a glass electrode and by pH meter.

Catalysts which can be used for the purposes of the present invention are catalysts which are suitable for hydrogenations and preferably comprise at least one metal of transition groups 8 to 12 of the Periodic Table of the Elements, e.g. Fe, Ru, Os, Co, Rh, Ir, Ni, Pd, Pt, Cu, Ag, An, Zn, Cd, Hg, preferably Fe, Co, Ni, Cu, Ru, Pd, Pt, particularly preferably Cu, preferably on a customary support material, particularly preferably on a support material comprising oxides of titanium, zirconium, hafnium, silicon and/or aluminum. The catalysts which can be used according to the present invention can be prepared by methods known from the prior art for preparing such supported catalysts. Preference is also given to using supported catalysts which comprise copper on an Al$_2$O$_3$— or TiO$_2$-containing support material in the presence or absence of one or more of the elements magnesium, barium, zinc or chromium. Such catalysts and their preparation are known from WO 99/44974.

Copper containing supported catalysts as described, for example, in WO 95/32171 and the catalysts disclosed in EP-A 44 444 and DE 19 57 591 are also suitable for the hydrogenation according to the present invention.

The hydrogenation can be carried out batchwise or continuously, for example in a tube reactor which is charged with a catalyst bed and in which the reaction solution is passed over the catalyst bed in, for example, the downflow or upflow mode, as described in DE-A 19 41 633 or DE-A 20 40 501. It may be advantageous to recirculate a substream of the reactor output, if appropriate with cooling, and pass it over the fixed bed of catalyst again. It can likewise be advantageous to carry out the hydrogenation in a plurality of reactors connected in series, for example in from 2 to 4 reactors, with the hydrogenation reaction being carried out to only a partial conversion of, for example, from 50 to 98% in the individual reactors upstream of the last reactor and the hydrogenation being completed only in the last reactor. It can be advantageous to cool the hydrogenation output from the preceding reactor before it enters the next reactor, for example by means of cooling facilities or by injection of cold gases, e.g. hydrogen or nitrogen, or by introducing a substream of cold reaction solution.

The hydrogenation temperature is generally in the range from 50 to 180° C., preferably from 90 to 140° C. The hydrogenation pressure employed is generally from 10 to 250 bar, preferably from 20 to 120 bar.

The hydrogenation can be carried out with addition of an inert solvent. Solvents which can be used include cyclic ethers such as THF or dioxane and also acyclic ethers, likewise lower alcohols such as methanol, ethanol or 2-ethylhexanol.

Otherwise, any hydrogenation methods can be employed and it is possible to use any hydrogenation catalysts as are customary for the hydrogenation of aldehydes and are described in detail in the standard literature.

EXAMPLE 1

Hydrogenation of Hydroxypivalaldehyde to Neopentyl Glycol

Hydrogenation Feed 1.1 mol of isobutyraldehyde were stirred with 1 mol of formaldehyde in the form of a 40% strength solution and 4 mol % of trimethylamine, based on isobutyraldehyde, at 75° C. for 1 hour. The reaction solution was concentrated by distilling off low boilers such as isobutyraldehyde and part of the water under atmospheric pressure. The bottoms obtained comprised 75% by weight of hydroxypivalaldehyde, 20% by weight of water and about 5% by weight of other organic secondary components.

Catalyst Used

Catalyst G as described in WO 95/32171 was used.

Hydrogenation

The mixture described above as hydrogenation feed served as starting solution. This mixture was brought to the pH indicated in each case in table 1 by addition of trimethylamine and was pumped over the catalyst in a hydrogenation reactor with circulation of liquid (recycle:feed=10:1) at a weight hourly space velocity of 0.3 kg$_{HPA}$/l$_{cat}$×h at 40 bar and 125° C. in the downflow mode. The conversion was completed in an after-reactor operated in a single pass at 40 bar and 125° C.

A comparison of the process of the present invention with comparative examples 1 and 2 in which the pH of the hydrogenation feed was in each case outside the range specified according to the present invention is shown in table 1.

The pH was measured using a Knick model 766 pH meter provided with a glass electrode N1041A from Schott.

TABLE 1

| Ex. | pH | HPA[2] [GC % by weight] | NPG[3] [GC % by weight] | i-BuOH[4] [GC % by weight] | HPN[5] [GC % by weight] | Acetal[6] [GC % by weight] | Selectivity |
|---|---|---|---|---|---|---|---|
| C1 | 5.3[1] | 0.03 | 91.97 | 2.63 | 0.92 | 0.43 | 96.71 |
| 1 | 7.4 | 0.02 | 93.04 | 2.10 | 0.90 | 0.11 | 97.83 |
| C2 | 8.3 | 0.07 | 91.89 | 3.08 | 1.04 | 0.09 | 96.62 |

[1]without addition of amine
[2]HPA = hydroxypivalaldehyde
[3]NPG = neopentyl glycol
[4]i-BuOH = isobutyl alcohol
[5]HPN = neopentyl glycol ester of hydroxypivalic acid
[6]Acetal = hydroxypivalaldehyde NPG acetal

We claim:

1. A process for the catalytic hydrogenation of methylolaikanals of the formula

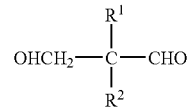

where R$^1$ and R$^2$ are each, independently of one another, a further methylol group or an alkyl group having from 1 to 22 carbon atoms or an aryl or aralkyl group having from 6 to 33 carbon atoms, in the liquid phase over a hydrogenation catalyst, wherein the pH of the hydrogenation feed is set to from 6.3 to 7.8 by addition of at least one tertiary amine.

2. The process according to claim 1, wherein the hydrogenation feed contains less than 5% by weight of formaldehyde.

3. The process according to claim 1, wherein a tri-n-alkylamine is used.

4. The process according to claim 1, wherein trimethylamine, triethylamine, tri-n-propylamine and/or tri-n-butylamine is/are used.

5. The process according to claim 1, wherein the hydrogenation catalyst comprises at least one metal of transition groups 8 to 12 of the Periodic Table of the Elements.

6. The process according to claim 1, wherein the hydrogenation catalyst is a supported catalyst.

7. The process according to claim 6, wherein the oxides of titanium, zirconium, hafnium, silicon and/or aluminum are used as support material.

8. The process according to claim 5, wherein the hydrogenation catalyst comprises copper on an Al$_2$O$_3$— or TiO$_2$-containing support material in the presence or absence of one or more of the elements magnesium, barium, zinc and chromium.

9. The process according to claims 1, wherein the methylolalkanal which is hydrogenated is hydroxypivalaldehyde, pentaerythrose or dimethylolalkanal.

* * * * *